United States Patent [19]

Lynn

[11] 4,283,495
[45] Aug. 11, 1981

[54] ROLLER BOTTLE

[75] Inventor: Robert W. Lynn, Oxnard, Calif.

[73] Assignee: Becton, Dickinson and Company, Paramus, N.J.

[21] Appl. No.: 123,957

[22] Filed: Feb. 25, 1980

Related U.S. Application Data

[62] Division of Ser. No. 949,450, Oct. 10, 1978, Pat. No. 4,238,568.

[51] Int. Cl.³ ............................................. C12N 5/00
[52] U.S. Cl. .................................................... 435/240
[58] Field of Search ............... 435/240, 241, 284, 285, 435/296, 312

[56] References Cited

U.S. PATENT DOCUMENTS

| | | | |
|---|---|---|---|
| 3,245,759 | 4/1966 | Eweson | 435/312 X |
| 3,338,795 | 8/1967 | McBee | 435/312 |
| 3,676,074 | 7/1972 | Shibayama et al. | 435/312 X |
| 3,740,321 | 6/1973 | Pagano et al. | 435/285 |

Primary Examiner—Esther M. Kepplinger

[57] ABSTRACT

A roller bottle is disclosed having a plurality of sections which may be bonded after their interior surfaces have been treated to enhance cell adhesion. The bottle may be plastic so that it is disposable, and has a pair of serrated circumferential edges to improve traction when in contact with rollers on a standard cell production roller apparatus. It includes a bottom cap, a cylindrical section, a top cap having a threaded neck, and a screw cap. The bottom and top caps include the serrated edges which enable the bottle to roll rather than slip on a roller apparatus. A method for the use of the bottles is also disclosed wherein a roller apparatus is able to rotate a large number of stacked bottles.

3 Claims, 3 Drawing Figures

U.S. Patent  Aug. 11, 1981  4,283,495
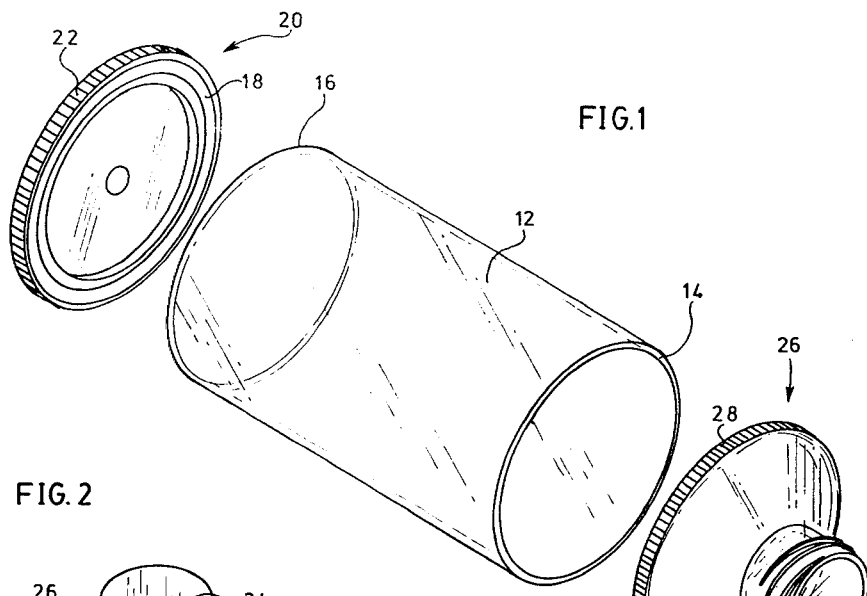
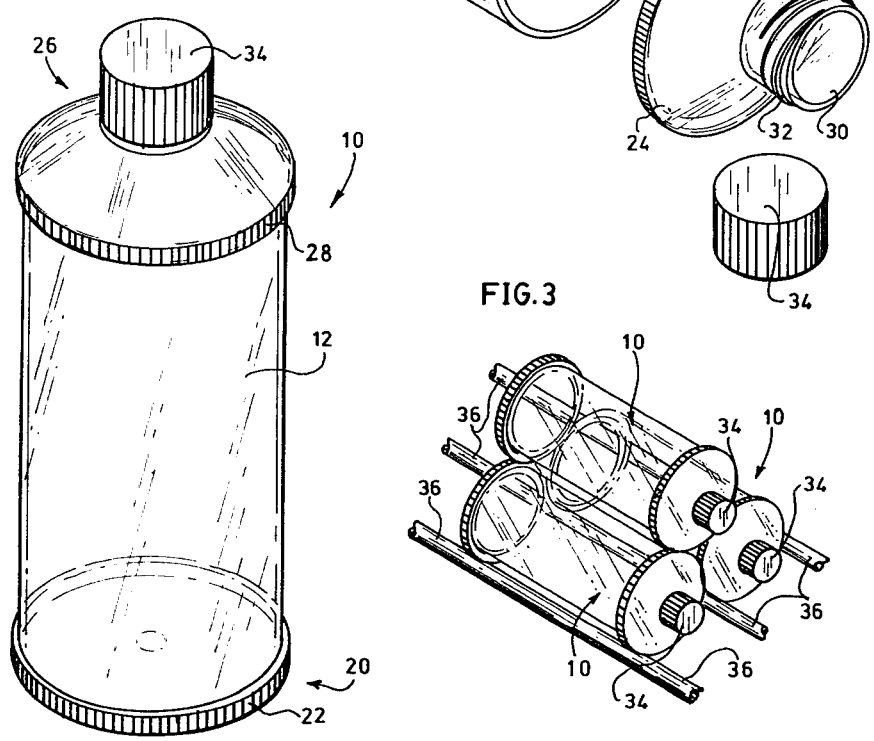

ROLLER BOTTLE

This is a division of application Ser. No. 949,450, filed Oct. 10, 1978, now U.S. Pat. No. 4,238,56800.

BACKGROUND OF THE INVENTION

1. Field of the Invention.

The field of the invention concerns roller bottles for cell growth production, their method of production, and their method of use.

2. Background of the Invention.

roller bottles have been widely used for the culturing of cells within the laboratory or other suitable locations. The bottles are placed on a standard cell production roller apparatus which rotates them at the desired speed. The interior surfaces of the bottles are preliminarily tissue culture treated using, for example, the corona discharge method. This improves the ability of cells to adhere to the surfaces.

Because the bottles usually have relatively narrow necks and are of one-piece construction, it has been difficult to obtain a uniformly treated interior surface to which cells may adhere. The corona discharge process works best when there is full access to a surface. The narrow neck of the bottle prevents such access as the treatment must be made through the neck. This results in uneven surface treatment and marginal cell adhesion.

Another problem with conventional roller bottles is that they will not roll on the roller apparatus unless they are either relatively heavy or a rubber band is wrapped around them to improve traction. Heavy bottles are relatively expensive and disadvantageous for this reason. The use of rubber bands is an inconvenience for the laboratory technician who must take the added time to apply them. They are also an added expense.

SUMMARY OF THE INVENTION

With the above-mentioned background in mind, it is one of the objects of the invention to provide a roller bottle having a uniformly treated interior surface.

It is another object of the invention to provide a roller bottle which is light, disposable and inexpensive, yet rotatable upon a standard roller apparatus without the need for rubber bands or the like.

Still another object of the invention is to provide a bottle which may be placed upon other bottles in pyrimidal fashion such that all will rotate when the rollers of a roller apparatus are actuated.

Still another object of the invention is to provide a roller bottle having a plurality of sections which may be welded together to form a bottle of desired size.

To accomplish these and other objectives, a roller bottle is provided having bottom and top end caps connected by a cylindrical center section. The top end cap may have a threaded neck to permit the attachment of a screw cap.

In production, the interior surfaces of the bottle sections can be tissue culture treated prior to assembly. A uniform surface is thereby provided for improving the adhesion of cells as one does not have to treat it through a neck portion.

The center section may be extruded and cut to any desired length. A bottle of any size internal capacity can accordingly be assembled. Present one piece roller bottle capacity is dependent upon length to diameter ratios possible in other fabrication technologies. The invention is not so dependent.

A plurality of serrated edges or rims are provided along the circumference of the exterior wall of the bottle. These edges may be positioned along the rims of the molded bottom and top end caps. When the bottle is placed upon a standard cell production roller apparatus, the edges provide improved traction as they contact the rollers. They also enable other bottles to be placed upon those contacting the rollers so that all of them rotate in unison.

BRIEF DESCRIPTION OF THE DRAWINGS

FIG. 1 is an exploded view of the invention;

FIG. 2 is a perspective view of the assembled bottle;

FIG. 3 is a perspective view of a plurality of roller bottles as they are rotated upon a roller apparatus.

DESCRIPTION OF THE INVENTION

The roller bottle 10 as shown in the drawings is assembled from a number of plastic parts as shown in FIG. 1. An extruded center section 12 of clear plastic is provided. The center section is substantially cylindrical in shape and has two open ends 14 and 16. Its interior surfaces can be tissue culture treated by any of several known methods such as corona discharge, liquid coating, or ozone injection prior to assembly. More uniform surface treatment for improved cell adhesion is thereby achieved than by treatment through a narrow neck of a bottle or a bottle which is closed at one end. By being extruded rather than blow molded, the center portion may be cut to any practical length to form a bottle of desired capacity.

One end 16 of the center section 12 is inserted into an annular groove 18 of a bottom end cap 20. The two parts are then permanently joined by ultrasonic welding, gluing, spin welding or the like. The bottom end cap 20 is provided with a serrated exterior rim 22, the serrations extending along the circumference of the cap. The opposite end 14 of the center section 12 is inserted into a corresponding annular groove 24 in top cap 26, then joined as previously described.

The top cap 26 has a serrated rim 28 similar to that of the bottom cap 20 and is somewhat conical in shape. It is provided with an integral, substantially smaller diameter neck 30 having integral external screw threads 32. To effect closure, an internally threaded screw cap 34 is utilized to mate with the threads on the neck 30. The screw cap 34 has a serrated exterior to facilitate gripping by the user. Both end caps and the screw cap may be molded or otherwise produced.

The assembled bottle is shown in FIG. 2. Due to the fact that the center section is inserted within the annular grooves of the end caps, the serrated rims 22 and 28 protrude beyond the body portion of the bottle.

The roller bottles are utilized for cell growth production by placing them on the rollers 36 of standard cell production roller apparatus as shown in FIG. 3. The rollers are rotated at a suitable speed as they contact the serrated portions of the bottles. Rotation without slippage is accordingly achieved.

An additional advantage of the invention is that the bottles may be stacked as shown in FIG. 3 such that the serrated portions of the upper bottles mesh with those of the lower ones. It will be observed that if the lower bottles in FIG. 3 are rotating in a clockwise direction, the upper bottle having serrated rims which mesh with those of the lower bottles will rotate in a counterclockwise direction. As one can readily appreciate, many more bottles than are shown in the drawing can be stacked in this pyramidal manner, thereby increasing the capacity of the roller apparatus. By providing serrated rims which protrude from the body portion of the bottles, excellent traction is obtained between the rollers 36 and the bottles and between stacked bottles. Full traction could also be insured if serrations were provided over the entire length of the bottles. Serrations in the form of V- or gear-shaped undulations are desirable as they insure both good traction and facilitate the inter-engagement of the bottles.

Those skilled in the art will appreciate that the roller bottle and its use herein described could be modified in a number of ways without departing from the spirit of the invention. The scope of the invention should accordingly be determined by reference to the appended claims.

What is claimed is:

1. A method for culturing cells within a roller bottle having an interior surface adapted for cell adhesion and an exterior surface including at least one serrated portion along its circumference comprising the steps of contacting said serrated portion with rollers of a roller apparatus and rotating said rollers whereby the bottle rotates without slipping.

2. A method as described in claim 1 wherein at least two serrated portions are provided on the exterior surface of the bottle, said serrated portions protruding from the exterior surface of the bottle.

3. A method as described in claim 1 wherein at least two bottles having at least one serrated portion are positioned upon rollers of a roller apparatus such that the serrated portions contact the rollers, and a third bottle having at least one serrated portion is stacked upon said at least two bottles such that the serrated portion of the third bottle meshes with the serrations of the bottles upon the rollers, whereby the rotation of the bottles upon the rollers also causes the third bottle to rotate.

* * * * *

REEXAMINATION CERTIFICATE (460th)

United States Patent [19]

Lynn

[11] B1 4,283,495

[45] Certificate Issued Feb. 11, 1986

[54] ROLLER BOTTLE

[75] Inventor: Robert W. Lynn, Oxnard, Calif.

[73] Assignee: Becton, Dickinson and Company, Paramus, N.J.

Reexamination Request:
No. 90/000,491, Jan. 23, 1984

Reexamination Certificate for:
Patent No.: 4,283,495
Issued: Aug. 11, 1981
Appl. No.: 123,957
Filed: Feb. 25, 1980

Related U.S. Application Data

[62] Division of Ser. No. 949,450, Oct. 10, 1978, Pat. No. 4,238,568.

[51] Int. Cl.$^4$ .............................................. C12N 5/00
[52] U.S. Cl. ................................................... 435/240
[58] Field of Search ............... 435/240, 241, 284, 285, 435/296, 312; 220/67, 85 SP; 366/208, 220, 233, 235; 51/164.1; 215/1 C, 10

[56] References Cited

U.S. PATENT DOCUMENTS

| 105,711 | 7/1870 | Miller | 366/233 X |
|---|---|---|---|
| D. 193,031 | 6/1962 | Hills | D58/8 |
| 951,978 | 3/1910 | Willson | 366/233 X |
| 2,741,402 | 4/1956 | Sayre | 220/67 X |
| 3,847,749 | 11/1974 | Smith et al. | 195/127 |
| 3,853,712 | 12/1974 | House et al. | 435/285 |
| 3,942,769 | 3/1976 | Whiteside et al. | 259/81 R |
| 3,971,167 | 7/1976 | van Moppes | 366/235 X |
| 4,045,918 | 9/1977 | Freedman | 366/235 X |
| 4,056,260 | 11/1977 | David | 366/144 |
| 4,201,306 | 5/1980 | Dubois et al. | 220/67 X |

OTHER PUBLICATIONS

Parker, *Method of Tissue Culture*, Third Edition, Hoeber Med. Div., Harper & Row, Publishers, New York, pp. 26-27 (1961).

*Primary Examiner*—Esther M. Kepplinger

[57] ABSTRACT

A roller bottle is disclosed having a plurality of sections which may be bonded after their interior surfaces have been treated to enhance cell adhesion. The bottle may be plastic so that it is disposable, and has a pair of serrated circumferential edges to improve traction when in contact with rollers on a standard cell production roller apparatus. It includes a bottom cap, a cylindrical section, a top cap having a threaded neck, and a screw cap. The bottom and top caps include the serrated edges which enable the bottle to roll rather than slip on a roller apparatus. A method for the use of the bottles is also disclosed wherein a roller apparatus is able to rotate a large number of stacked bottles.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–3 are cancelled.

* * * * *